United States Patent
Akiyama et al.

(10) Patent No.: US 8,276,469 B2
(45) Date of Patent: Oct. 2, 2012

(54) STACK-GAS MEASURING APPARATUS AND STACK-GAS MEASURING METHOD

(75) Inventors: Shigeyuki Akiyama, Otsu (JP); Atsushi Yamamoto, Otsu (JP); Takuji Oida, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 531 days.

(21) Appl. No.: 12/550,205

(22) Filed: Aug. 28, 2009

(65) Prior Publication Data
US 2010/0050790 A1    Mar. 4, 2010

(30) Foreign Application Priority Data

Aug. 29, 2008 (JP) .................................. 2008-221934

(51) Int. Cl.
*G01N 1/22* (2006.01)
(52) U.S. Cl. .................................................. 73/863.23
(58) Field of Classification Search ............... 73/863.23, 73/863.81
See application file for complete search history.

(56) References Cited

U.S. PATENT DOCUMENTS
5,571,946 A * 11/1996 Koshi et al. ................... 73/28.01

FOREIGN PATENT DOCUMENTS
JP    01094920 A   *   4/1989
JP    2006-226866       8/2006

OTHER PUBLICATIONS

Automated Measuring Systems and Analyzers for Nitrogen Oxides in Flue Gas (article), Japanese Standards Association Web Store, Apr. 30, 2002, 25 pages, Japan Electric Measuring Instruments Manufacturers' Association, Japan.

* cited by examiner

*Primary Examiner* — Peter Macchiarolo
*Assistant Examiner* — Tamiko Bellamy
(74) *Attorney, Agent, or Firm* — Alleman Hall McCoy Russell & Tuttle LLP (57) ABSTRACT

A stack-gas measuring apparatus includes a sample introducing unit (sampling unit and heating conduit pipe) for introducing stack-gas, a cooling unit (containing wet filter) in which dust components in the stack-gas are agglomerated, a filter column containing a filter element made of a polymer material for collecting the dust components, a mist scrubber which is disposed downstream of the filter column and which contains an adsorbent for removing acid mist in the stack-gas, and an analyzer in which the cleaning-processed gas is introduced to measure a particular component in the stack-gas.

5 Claims, 6 Drawing Sheets

Prior Art

STACK-GAS MEASURING APPARATUS AND STACK-GAS MEASURING METHOD

TECHNICAL FIELD

The present invention relates to an apparatus and a method for measuring a stack-gas containing dust components such as fly ash, for example, and to a stack-gas measuring apparatus and a stack-gas measuring method for measuring the stack-gas containing dust components, acid mist, halogen components, etc. from a boiler of a diesel electric power generator, a glass fusion furnace, etc.

BACKGROUND

Figure 8:
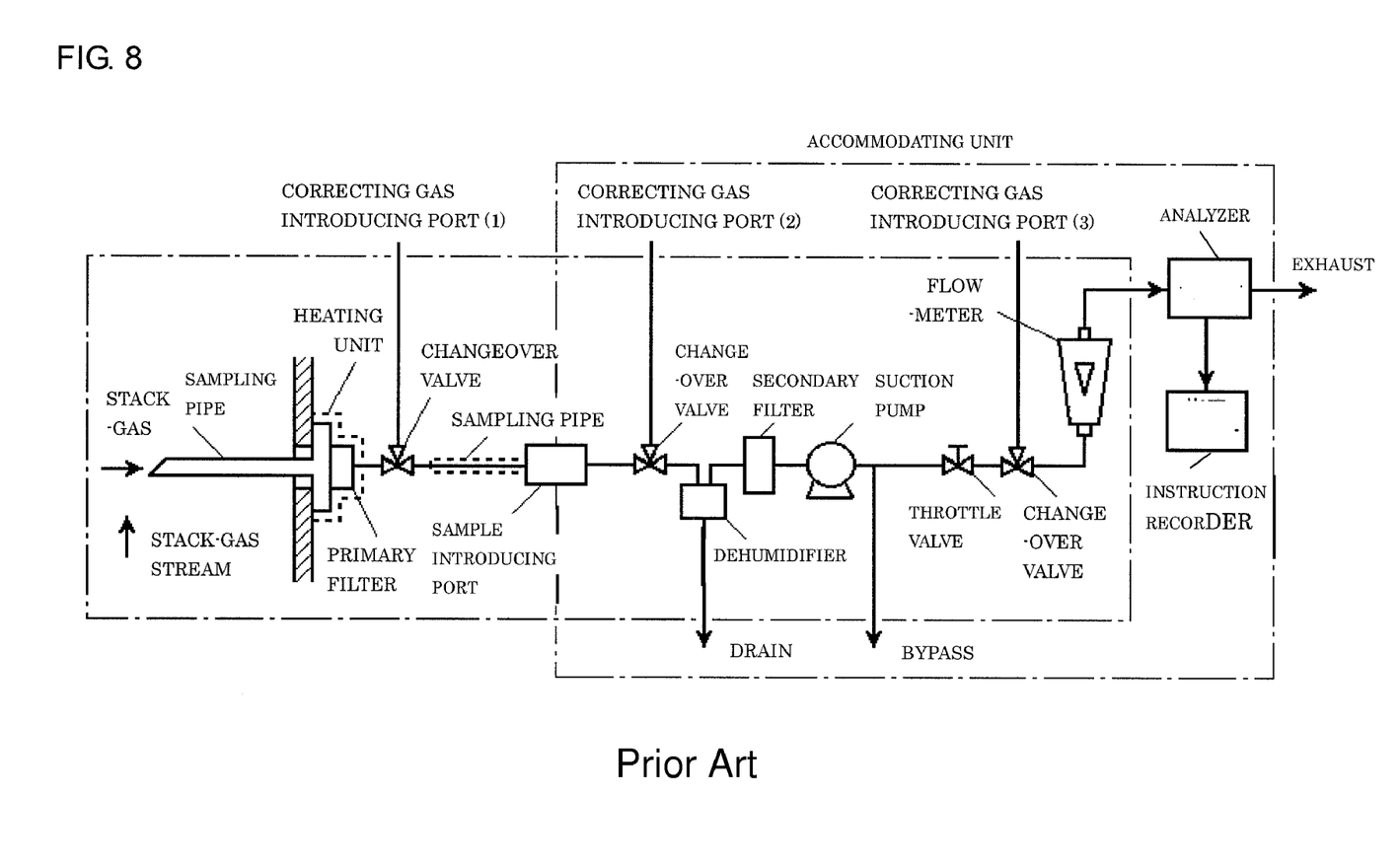
FIG. 8 is a diagram schematically showing the construction of an analyzer according to a prior art.

As shown in FIG. 8, in order to dehumidify a sample fluid, remove dusts from the sample fluid, keep the flow rate of the sample fluid constant, etc. in a passage from a sample extracting point to an analyzer, a conventional atmospheric pollution measuring apparatus such as a measuring apparatus for a source of gas outbreaks, an ambient air measuring apparatus, a vehicle exhaust gas measuring apparatus or the like is provided with a filter, a changeover valve, a sampling pipe, a dehumidifier, a suction pump, a throttle valve, a flowmeter, etc., and also the respective members are connected to one another through pipes to form a sample flow passage (see Japanese Industrial Standards "JIS B7982-2002", for example).

Figure 9:
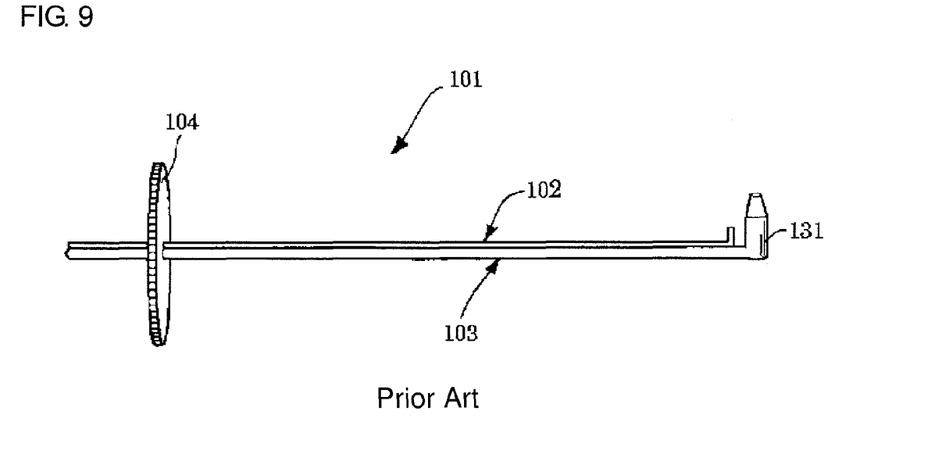
FIG. 9 is a diagram schematically showing the construction of a sampling device according to the prior art.

There has been also proposed, as shown in FIG. 9, a stack-gas sampling apparatus 101 in which a time required for measuring the concentration of funnel fume (soot and smoke) can be shortened by simultaneously extracting solid components such as ash dust (soot and dust) in the stack-gas and gas components such as sulfur oxides ($SO_x$) and nitrogen oxides ($NO_x$). In this stack-gas sampling apparatus 101, a sampling probe 102 for measuring gas components and a sampling probe 103 for measuring ash dust are arranged in parallel and in proximity to each other by a tap member 104 having openings through which these sampling probes 102 and 103 can be inserted. The insertion length of at least one of the sampling probes 102 and 103 into a gas duct can be adjusted. A filter (not shown) can be installed in or connected to the sampling probe 102 for measuring the gas components, and a dust collector 131 can be also installed in or connected to the sampling probe 103 for measuring the ash dust (see JP-A-2006-226866, for example).

However, the foregoing measuring apparatuses have had some problems. That is, stack-gas from a glass fusion furnace, a boiler of a diesel electric power generator, a metal refining incinerator, a refuse incinerator, an iron and steel fusion furnace, etc. (hereinafter referred to as "high-temperature fusion furnace, etc.") contains acid mist which is a corrosive substance, such as $SO_3$ mist. Accordingly, when stack-gas is measured by using the foregoing measuring apparatuses, acid mist has been hitherto removed by using a column containing inorganic porous material or granular activated charcoal impregnated with nonvolatile acid in a sample treatment unit. However, it has been defective in long-term stability, and the reason for this has been unclear.

SUMMARY

Therefore, in view of the foregoing problems, various embodiments are disclosed herein that have an object to provide a stack-gas measuring apparatus and a stack-gas measuring method with which a continuous measurement can be performed on even a high-temperature fusion furnace, etc. with high long-term stability without being affected by dust components and acid mist contained in the stack-gas.

As a result of repetitive enthusiastic studies, the inventor has found the following matters and implements the present invention by a stack-gas measuring apparatus and a stack-gas measuring method, such as in the example embodiments described below.

That is, dust components such as so-called micro-dust of 2 μm or less, or fly ash, are contained in stack-gas from a high-temperature fusion furnace or the like. Therefore, these components cannot be removed by a normally-used primary filter provided at the sample extracting point, and thus brought into a sample treatment unit. At this time, these dust components are bonded to acid mist, which causes pollution, corrosion, etc. of a flow passage and also induces degradation of removing capability in the mist removing column described above. That is, it has been found through an inspection process that dust components and acid mist contained in stack-gas as described above have much effect on the sample processing of the stack-gas measuring apparatus through composite action.

The present disclosure based on this novel knowledge targets stack-gas containing dust components such as fly ash and acid mist such as $SO_3$ mist, as a measurement target sample, and is characterized by comprising: a sample introducing unit for introducing the stack-gas; a cooling unit in which dust components are agglomerated; a dust collecting unit for collecting dust components to be agglomerated in the cooling unit; a mist collecting unit which is provided downstream of the dust collecting unit and which contains an adsorbent for removing acid mist from the stack-gas; and an analyzer into which treatment gas clean-treated by the above units is introduced to measure a kind of component in the stack-gas.

That is, when dust components such as micro-dust or fly ash are contained as in the case of stack-gas from a glass fusion furnace or the like, it has been found that by providing the cooling unit to a sample treatment unit, gaseous water is liquefied, the liquefied water and the dust components are agglomerated so as to be collected in the dust collecting unit (filter), and the water agglomerated in the cooling unit adheres to the surface of the filter so that the filter surface is kept in a humidified state, whereby fine particle materials (for example, 2 μm or less) such as micro-dust can be collected without separately providing any precision filter or the like. Furthermore, it has been also found that the dust components and the acid mist contained in the stack-gas compositely induce not only pollution of a flow passage, but also degradation of an acid mist removing capability due to pollution of the column. According to the present disclosure, as a test result as to how effectively the dust components described above can be removed, it has been found that stack-gas containing water from the sample introducing unit is passed through the dust collecting unit containing a filter element comprising a polymer material, whereby the dust components in the stack-gas can be collected with an extremely high yield. That is, it has been found that it is difficult to perfectly collect micro-dust of 1 μm or less by using an inorganic filter comprising glass wool, ceramics or the like which has been hitherto frequently used, but an element having a surface material which can keep a humidified state on the filter surface, such as nonwoven fabric or a fibrous material made of polyester, polypropylene or the like, as described later, has a high collecting capability. Accordingly, not only the dust components can be removed, but also deterioration of the acid mist removing unit disposed at the rear stage can be prevented.

A column containing an inorganic adsorbent as a main component such as perlite, as described above, functions sufficiently as the acid mist removing unit under the state that the dust components as described above are sufficiently removed. However, according to the present disclosure which targets stack-gas containing a high concentration of acid mist, the removal of the acid mist can be performed more efficiently and used for a long term by using an adsorbent which is subjected to a nonvolatile acid impregnating treatment, for example, granular activated charcoal impregnated with phosphoric acid. Accordingly, there can be provided a stack-gas measuring apparatus which can perform continuous measurements having high long-term stability without being affected by dust components, acid mist, etc. contained in the stack-gas. By the nonvolatile acid impregnating treatment, stability of the adsorbent can be secured, loss of $SO_2$, $NO_x$, etc. as measurement target components in the stack-gas due to adsorption can be prevented, and also loss of active charcoal, etc. due to burning under the heating condition can be prevented.

Here, "dust components" include dust causing components which possibly become dusts such as metal oxides or metal salt-containing components, which may also exist in a vaporization state under a high-temperature condition, micro-dust of 2 μm or less, submicron fly ash containing combustion ash as a main component, etc. or a mixture thereof. Furthermore, "acid mist" includes gaseous $SO_3$, $SO_3$ mist, nitric acid mist, water, combinations of these materials with the dust components and a mixture of these materials. Further still, "cooling unit" is not limited to an individual member such as a wet filter described later insofar as it performs a cooling function on the sample gas in order to have dust components agglomerated. For example, this is assumed to have a broad concept containing a part of the sample introducing unit and the dust collecting unit which has these functions.

Furthermore, in some embodiments, the stack-gas measuring apparatus described above has the dust collecting unit functioning as a monitor of the pollution state of the dust components and a mist monitor containing adsorbent downstream of the mist collecting unit.

That is, in the stack-gas measuring apparatus in which the long-time continuous operation is frequently carried out, it is preferable to monitor conditions such as pollution of the sample treatment unit with respect to dust components and acid mist. Here, stack-gas from a glass fusion furnace contains lots of colored dust components. Accordingly, the coloring state of the dust collecting unit as described above is utilized as a monitor of the pollution condition thereof according to the present disclosure. That is, the dust collecting function of the dust collecting unit and the function as the dust monitor are used. Specifically, for example, a dust component removing unit is disposed in series, and the coloring state at the upstream side is monitored. In addition, the column is exchanged with a coloring start time at the downstream side being set as an exchange timing, whereby the further downstream side is prevented from being affected and it is possible to make the assurance of the function doubly sure. Even when the dust components themselves are not colored, the dust collecting unit may contain a component which can react with a particular component contained in the dust components to turn color or subjected to a surface treatment using the component concerned, whereby the function as the dust monitor can be likewise secured. With respect to colorless dusts, water droplets, acid mist, etc. adhere to dusts collected by the dust collecting unit and an occurrence of foreign materials is checked at the scene. Accordingly, by checking the occurrence state of foreign materials as described above, the function as the dust monitor can be secured. Furthermore, with respect to the acid mist, it is known that acid mist adsorbed to an inorganic adsorbent such as perlite is gradually bonded with coexisting water and becomes droplets, and thus the acid mist droplets adhere to the surface of the adsorbent or the inner surface of the column containing the adsorbent. According to the present disclosure, the adhesion state of the droplets in the column as described above is used as a monitor of the pollution condition of the mist collecting unit. In addition to the function of the monitor, the influence on the further downstream side is prevented by the acid mist removing capability of the mist monitor itself, so that it is possible to make the assurance of the function doubly sure.

In the stack-gas measuring apparatus according to the present disclosure, even when halogens such as hydrogen fluoride or halides are contained in the stack-gas, a halogen collecting unit containing, and in some embodiments filled with, an element which is made of a metal material for removing halogens or halides and subjected to a surface treatment based on nonvolatile acid is disposed downstream of the mist collecting unit or the mist monitor, and a halogen monitor containing, and in some embodiments filled with, an element formed of porous material containing coloring material is disposed downstream of the halogen collecting unit.

As described above, the stack-gas from the glass fusion furnace or the like may contain not only dust components and acid mist, but also halogen components. These materials are components having strong corrosion behavior and may also exert a composite harmful influence by reaction with metal oxides in the dust components or dissolution into droplets formed from acid mist. Furthermore, with respect to the halogen components, halogens such as fluorine or chlorine and halides such as hydrogen fluoride or hydrogen chloride have different characteristics, but they are required to be treated likewise. According to the present disclosure, high reactivity of halogens with metal material such as copper or tin is utilized, and this is used as the halogen collecting unit. The halogen components can be efficiently and selectively removed as a whole. The loss of $SO_2$, $NO_x$, etc. as measurement target components in the stack-gas can be prevented by the nonvolatile acid impregnating treatment. Furthermore, a porous material which is subjected to an impregnation treatment of silver salt to generate a colored compound through reaction with halogen is disposed downstream of the halogen collecting unit, whereby it can be used as a monitor for the pollution condition of the halogen collecting unit. In addition, the influence on the further downstream side can be prevented by the halogen-compound removing capability of the halogen monitor itself, whereby it is possible to make the assurance of the function doubly sure.

According to the stack-gas measuring apparatus of this disclosure, even when halogens or halides such as hydrogen fluorine are contained in the stack-gas, a halogen collecting unit for removing the halogens or halides is provided upstream of the mist collecting unit.

In a case where a lot of halogens or halides such as hydrogen fluorine are contained in stack-gas, when there exists fine dust components (particularly, metal compounds or the like) in sample gas introduced into the mist collecting unit, it causes degradation of the collecting capability of the mist collecting unit through generation or growth of metal halogen compounds or the like. Accordingly, it is preferable to dispose the halogen collecting unit upstream of the mist collecting unit in the case of some kinds of stack-gas compositions. As described later, the halogen collecting unit according to the present disclosure also has the function of removing the mist components, and thus the halogen components and the mist components can be simultaneously removed in the halogen collecting unit by disposing the halogen collecting unit upstream of the mist collecting unit. Accordingly, the load of the mist collecting unit provided at the downstream side can be reduced. Particularly, when high mist stack-gas is targeted, an embodiment according to the present disclosure is suitably used because it greatly contributes to an increase of the lifetime of the mist collecting unit and long-term stability of the overall system. Furthermore, in some embodiments, the halogen collecting unit and the halogen monitor function integrally with each other. According to the present disclosure, the sample treatment is suitably executed in accordance with the use condition of the stack-gas measuring apparatus such as the stack-gas composition, etc., whereby the continuous measurement having high long-term stability can be performed.

According to the present disclosure, stack-gas containing dust components such as fly ash, and acid mist such as $SO_3$ mist or these materials and halogens or halides such as hydrogen fluorine is targeted as the measurement target sample, and sampled stack-gas are subjected to a primary treatment to collect the dust components under coexistence with water by the dust collecting unit and subjected to a secondary treatment to remove the acid mist by the mist collecting unit. Stack-gas containing halogens or halides is subjected to a tertiary treatment to remove the halogens or halides by the halogen collecting unit, and a particular component in the processed gas which has been subjected to the primary and secondary treatments or the primary to tertiary treatments is measured.

In the measurement of the specific component in the stack-gas containing the dust components and the acid mist or the stack-gas containing not only the dust components and the acid mist, but also halogen components, gas from which these components are efficiently and selectively removed without any loss of the specific component and cleaned is required to be introduced into the analyzer. At this time, the respective components such as dust components, or halogen components may exercise not only individual effects, but also composite effects, and it is necessary to pay attention to the removing method so as to prevent occurrence of the composition function. According to the present disclosure, dust components nucleating with respect to various chemical reactions or physical phenomena in the respective components are first removed to facilitate the treatments at the subsequent stages (primary treatment), the acid mist is then targeted as a main treatment target, and the mist collecting unit which also has a treatment effect on halogen components (secondary treatment) is used, thereby providing a stack-gas measuring method which can perform continuous measurement having high long-term stability. Furthermore, when halogen components are contained in stack-gas, the treatment is executed by using the efficient and selective halogen collecting unit (tertiary treatment), there can be provided a stack-gas measuring method which can perform a continuous measurement having high long-term stability in a broad range.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure

DETAILED DESCRIPTION

Various embodiments according to the present disclosure will be described with reference to the accompanying drawings.

A stack-gas measuring apparatus according to the present disclosure (hereinafter referred to as "this apparatus") targets stack-gas containing dust components and acid mist as a measurement target sample, and it is provided with (1) a sample introducing unit, (2) a cooling unit in which the dusts are agglomerated, (3) a dust collecting unit for collecting the dust components, (4) a dust monitor for monitoring the pollution condition of the dust collecting unit, (5) a mist collecting unit for removing acid mist, (6) a mist monitor for monitoring the pollution condition of the mist collecting unit, and (9) an analyzer for measuring a particular component. When halogen components are contained in stack-gas, the stack-gas measuring apparatus is further provided with (7) a halogen collecting unit for removing the halogen components and (8) a halogen monitor for monitoring the pollution condition of the halogen collecting unit.

<Basic Construction of Stack-Gas Measuring Apparatus According to the Present Disclosure>

Figure 1:
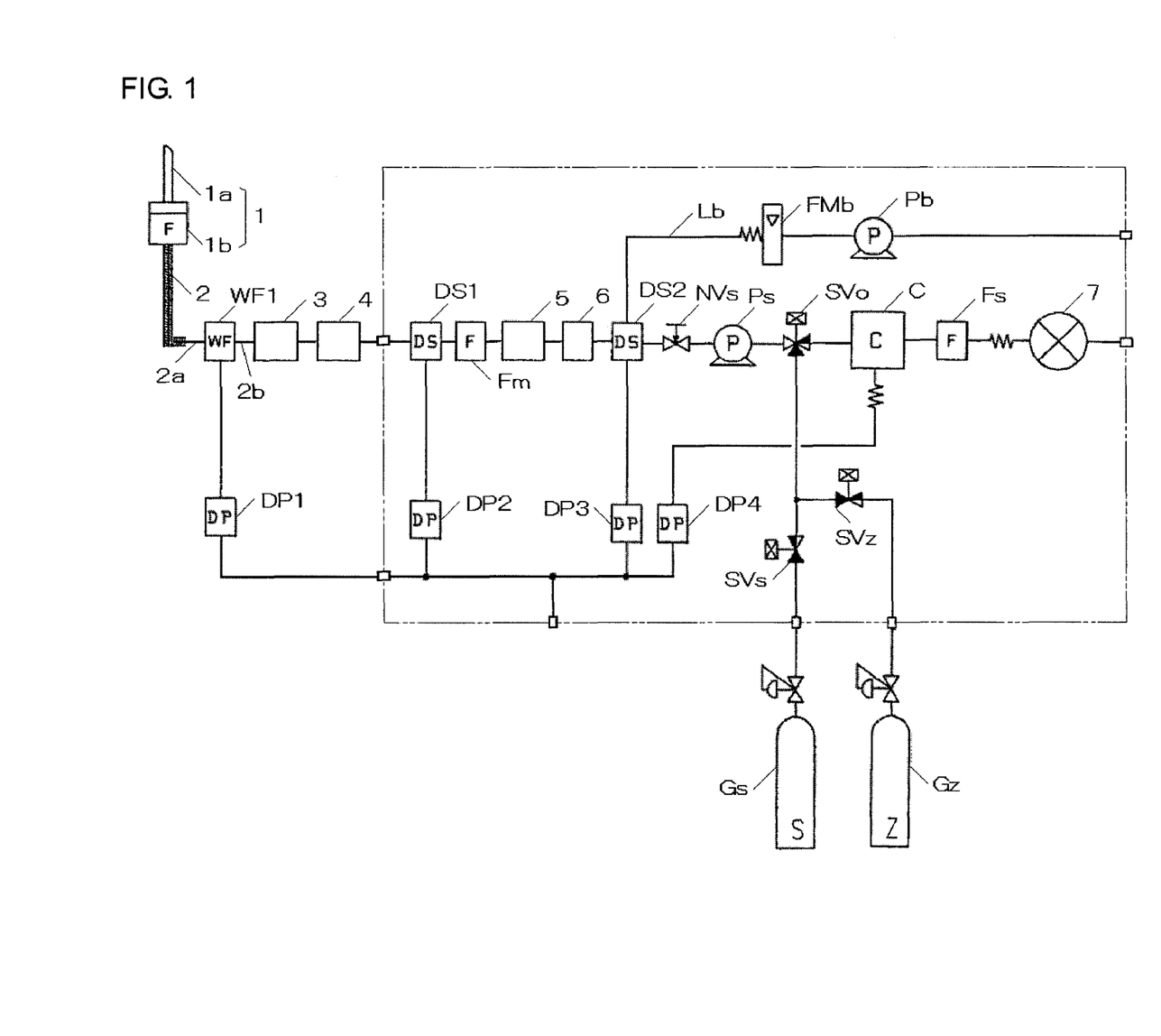
FIG. 1 is a diagram showing a basic construction of a stack-gas measuring apparatus according to the present disclosure.

The basic construction of this apparatus is shown in FIG. 1 (first construction example). Sample gas (stack-gas) extracted at a sampling unit 1 provided in a duct (not shown) through which the stack-gas flows is passed through a heating conduit pipe 2 (corresponding to a sample introducing unit together with the sampling unit 1) provided just at the rear stage of the sampling unit 1 and introduced into a wet filter WF1 (corresponding to a cooling unit together with a subsequent pipe portion). The dust components are agglomerated in the wet filter WF1, and sample gas containing the agglomerated dust components is introduced into a filter column 3 (corresponding to a dust collecting unit, and which may correspond to the dust collecting unit together with a dust monitor 4 described later). Drainage separated in the wet filter WF1 is discharged through a drain pot DP1 to the outside. The sample gas from which the dust components are collected is introduced through the dust monitor 4 into a drain separator DS1. The drainage separated in the drain separator DS1 is discharged through a drain pot DP2 to the outside. On the other hand, the sample gas from which the drainage is separated is introduced through a precision filter Fm into a mist scrubber 5 (corresponding to a mist collecting unit) to remove acid mist. In the precision filter Fm, dust components of, for example, 1 μm or less which are contained in stack-gas or occur in connection with the cooling treatment or occurrence of drainage are removed. The sample gas from which the acid mist is removed in the mist scrubber 5 is introduced through a mist monitor 6 into a drain separator DS2. In the drain separator DS2, newly occurring drainage is separated, and also the sample gas from which the drainage is separated is introduced through an adjusting valve NVs, a suction pump Ps, a changeover valve SVo, an electric cooler C and a second filter Fs into an analyzer 7 while a part of the sample gas is discharged from a bypass flow passage Lb. The drainage separated in the drain separator DS2 is discharged through a drain pot DP3 to the outside, and drainage occurring in the electric cooler C is discharged through a drain pot DP4 to the outside. Bypass gas is discharged through a flowmeter FMb and a suction pump Pb.

Furthermore, in this apparatus, high-pressure containers (a zero gas container Gz and a span gas container Gs) filled with correcting gas are connected to one port of the changeover valve SVo through opening/closing valves SVz and SVs. The zero correction of the analyzer is carried out while the changeover valve SVo and the opening/closing valve SVz are set to an open state, and the span correction of the analyzer is carried out while the changeover valve SVo and the opening/closing valve SVs are set to an open state.

Here, stack-gas targeted as the measurement target sample by this apparatus is, for example, stack-gas from a glass fusion furnace, a boiler of a diesel electric power generator, a metal refining incinerator or the like, and it is required to treat dust components and acid mist or treat halogen components together with the dust components and the acid mist mainly. The dust components contain dust-causing components which possibly become dusts such as metal oxides, or metal salt-containing components which are vaporized under a high-temperature condition, micro-dust of 2 μm or less, for example, fly ash of sub micron containing combustion ash or the like as a main component, or a mixture of these materials. The acid mist contains gaseous $SO_3$, $SO_3$ mist, nitric acid mist, water, combinations of these materials with the dust components and a mixture of these materials. One of the harmful materials may contain halogens such as fluorine ($F_2$) or chlorine ($Cl_2$), and halides such as hydrogen fluorine (HF) or hydrogen chloride (HCl), combinations of these materials with the dust components, or a mixture of these materials (halogen components).

The sampling unit 1 comprises a sample extracting pipe 1a and a primary filter 1b. Sample gas is sucked and extracted from the sample extracting pipe 1a inserted in the duct, and dusts are removed from the sample gas by the primary filter 1b. However, when stack-gas can be extracted under the state that dusts are sufficiently removed by an electric dirt collector (EP), the primary filter 1b may be omitted. This is effective in a case where a low concentration of $SO_2$, which is lost due to adsorption or dissolution or easily affected by response delay, is measured. The inside of the duct is set to a high-temperature state of about 300 to 400° C. as described above. Therefore, by directly extracting the sample gas, the temperature of the sampling unit 1 can be kept to a high temperature of 200° C. or more. In this case, it is not required to separately provide a heating unit for the sampling unit 1, however, it is preferable to provide a heating unit as a complementary unit in the winter season or at a cold district. The sample gas from which dusts are removed is introduced through the heating conduit pipe 2 into the wet filter WF1. In the heating conduit pipe 2, the sample gas is heated to the extent that water in the sample gas is not condensed (about 100 to 120° C.).

Furthermore, in this apparatus, the dust components are divisionally treated at three stages by using the primary filter 1b, the filter column 3 (containing the dust monitor 4) and the precision filter Fm, whereby the dust components can be efficiently treated, and also factors for disturbing removal of the mist components and the dust components which have been hitherto unclear can be reduced. With respect to the style, number and amount of each unit, they can be suitably set in accordance with the property of the sample gas.

Specifically, a filter for collecting large granular dusts (for example, 2 μm or more) under a heat state (150 to 200° C.) is used as the primary filter 1b, a filter for collecting micro-dust (for example, 2 μm or less) under a low temperature state (for example, normal temperature) (described later in detail) is used as the filter column 3, and a filter for collecting micro-dust (for example, 1 μm or less) which cannot be collected by the filter 1b and the filter column 3 under a low temperature state (for example, normal temperature) is used as the precision filter Fm, whereby the loads imposed on the respective filters can be set in accordance with the respective functions thereof. Furthermore, the filter column 3 is disposed downstream of the wet filter WF1. Accordingly, the agglomerated dust components can be effectively collected, and the filter is used under a condition that the filter surface is set to a humidified state, whereby micro-dust (for example, 2 μm or less) passing through the primary filter 1b and a large amount of fly ash can be effectively collected. Therefore, these dust components can be prevented from flowing to the precision filter Fm disposed at the downstream side and clogging it, and the load thereof can be reduced. Here, the dust components are sorted by using the particle size (average particle diameter, the maximum particle diameter or the like) as an indication for processing targets. For example, the dusts of 2 μm or less are defined as micro-dusts (for example, 2 μm or less). When the dust components are required to be more finely sorted, the dust components are defined "micro-dust (for example, 1 μm or less)", "micro-dust of 0.1 μm, for example" or "micro-dust of 0.01 μm or more".

The analyzer 7 is selected in accordance with the measurement target component in stack-gas. $NO_x$, $SO_2$, carbon monoxide (CO), oxygen ($O_2$), etc., which are determined on the basis of the effluent standard, are generally targeted. An infrared type analyzer, an ultraviolet type analyzer or the like is used for is used for $NO_x$, $SO_2$ and CO, and a magnetic type oxygen meter or the like is used for $O_2$.

[Cooling Unit]

This apparatus is characterized by comprising a cooling unit in which dust components are agglomerated and a dust collecting unit in which the agglomerated dust components are collected. In the construction shown in FIG. 1, a wet filter WF1 or pipe portions 2a and 2b which are connected to the wet filter WF1 under a normal temperature state are provided upstream of the filter column 3. Not only the filter column 3, but also the inside of the dust monitor 4 has a cooling function for making the dust components agglomerated, and thus the dust collecting unit is also contained in the cooling unit of this apparatus. Gaseous water in the sample gas is liquefied and micro-dust components are agglomerated together through the liquefied water, so that the micro-dust components are adjusted to have such a size that they can be easily collected. Accordingly, they can be efficiently collected by the filters such as the filter column 3 provided downstream of the cooling unit. Furthermore, stack-gas containing micro-dust components such as metal oxides or metal salt-containing components which are vaporized under a high-temperature state (for example, 1200° C. or more) is cooled to a low temperature (containing normal temperature, for example) to crystallize or agglomerate the micro-dust components, whereby the solidified micro-dust components can be collected.

Figure 2:
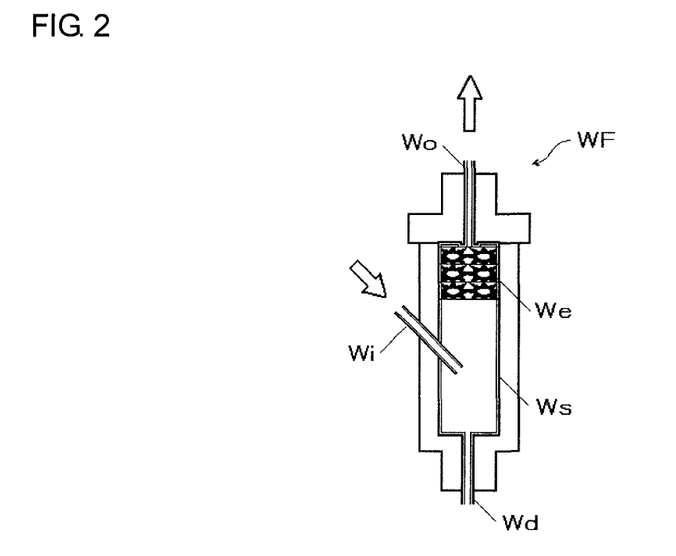
FIG. 2 is a diagram showing an example of a member constituting a cooling unit used in a sample processing system according to the present disclosure.

The wet filter WF has a structure as shown in FIG. 2, for example, and has both a cooling function and a gas-liquid separating function. When it is provided with a filter element We, it can have a dust collecting function. Sample gas is introduced from an introducing port Wi into a space portion Ws to be cooled, and drainage occurring in the pipe portion 2a and the space portion Ws is subjected to gas-liquid separation. The drainage is discharged from a drain port Wd (through a drain pot DP), and the sample gas separated from the drainage is fed from a feed-out unit Wo to the filter column 3, etc. at the downstream side. At this time, when the filter element We is provided, newly occurring dust components which are agglomerated by the cooling of the pipe portion 2a and the space unit Ws can be removed. Furthermore, in some embodiments, the filter element We comprises a fibrous material made of polymer material or non-woven cloth as in the case of a filter element 3a filled in the filter column 3 as described later.

Figure 3:
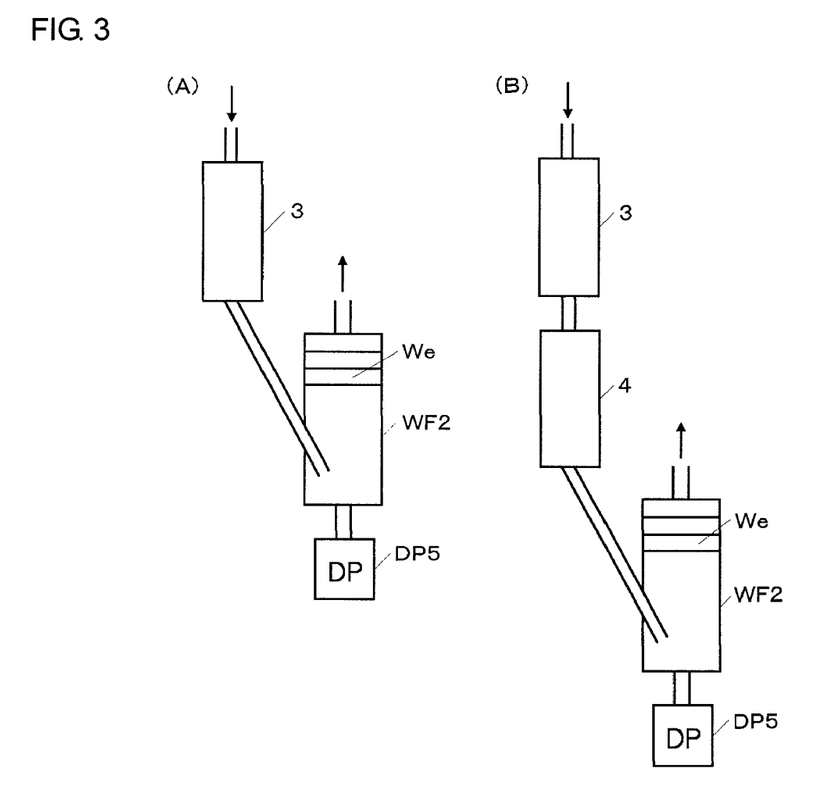
FIGS. 3A and 3B are diagrams showing an example of the construction of the sample processing system according to the present disclosure, respectively.

In FIG. 1, the cooling unit comprising the pipe portion 2a, the wet filter WF1 and the pipe portion 2b is provided, and the filter column 3 as the filter collecting unit is provided downstream of the cooling unit. Furthermore, the cooling unit is provided downstream of the filter column 3 in some embodiments. When the amount of water in stack-gas is large, the pipe temperature is increased to prevent the clogging of the heating conduit pipe 2 in some cases, and it is suitably applied to a case where the cooling efficiency is low under a high-temperature state, like the summer season. Specifically, there may be adopted a construction that a wet filter WF2 is provided downstream of the filter column 3 as shown in FIG. 3A and a construction that the wet filter WF2 is provided downstream of the filter column 3 and the dust monitor 4 as shown in FIG. 3B. These constructions have the cooling function and also the gas-liquid separating function and the dust collecting function for condensed water occurring in the filter column 3 and the dust monitor 4 and the agglomerated dust components, and can keep the filter column 3 and the dust monitor 4 to a proper humid state.

[Filter Column]

Figure 4:
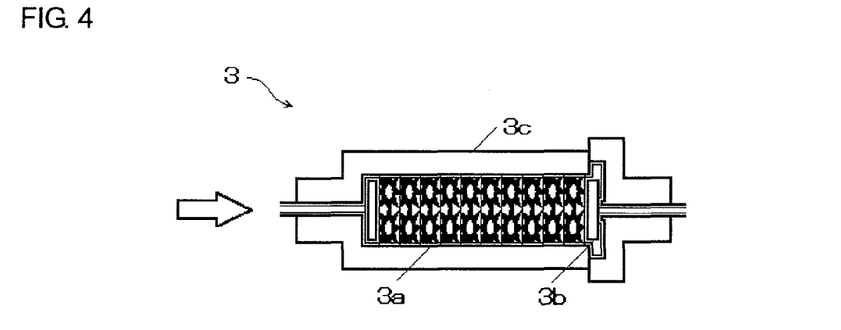
FIG. 4 is a diagram showing an example of the construction of a dust collecting unit used in the sample processing system according to the present disclosure.

The filter column 3 is a unit containing, and in some embodiments filled with, a filter element made of polymer material. Specifically, it is preferably constructed so that filter elements 3a, each of which is formed of a fibrous material or non-woven cloth, are stacked at plural stages as shown in FIG. 4. A non-linear gas stream is formed in the filter element 3a, so that the contact time between the gas stream and the surface of the filter element 3a can be increased. Therefore, a high collecting capability of micro-dust of 0.1 µm or less and fly ash can be secured, for example. Here, with respect to the mesh-like filter element formed of nonwoven cloth or the like, in some embodiments, it can collect dust components having a predetermined particle diameter of 0.1 µm or more, for example. The distance by which sample gas passes through the inside of the filter element is short, and the collecting capability of dust under the humidified state is not large. Therefore, it is preferable to reduce the particle diameter of particles which can be collected.

On the other hand, with respect to the fibrous type filter element, in some embodiments, it has a predetermined collecting rate, for example, a collecting rate of 50% or more defined in JIS-Z8901. At this time, the particle-diameter range of dust components which can be collected by the filter element of the polyester material is also broad and, for example, the particle diameter distribution is as follows: 0 to 5 µm: 39%, 5 to 10 µm: 18%, 10 to 20 µm: 16%, 20 µm or more: 27%. Since the non-linear gas stream as described above can be formed, and the contact time between the gas stream and the surface of the filter element 3a can be increased, the dust collecting capability under the humidified state is high. Furthermore, the filter element formed of the fibrous material and the filter element formed of the non-woven cloth may be mixed with each other to secure the excellent characteristics of both the filter elements. Further still, the effect of the dust components on the removing treatment of acid mist at the subsequent stage which has been hitherto the problem can be greatly reduced and overcome, so that the lifetime of the mist scrubber 5 can be lengthened and the long-term stability of the overall system can be secured.

In the case of the sample flow rate of 1 to 10 L/min, the filter column 3 is shaped to have a diameter of 10 to 50 mm, more preferably about 30 to 50 mm, a length of 10 to 150 cm, more preferably about 15 to 25 cm, and a volume of 10 to 8000 cm$^3$, more preferably 100 to 500 cm$^3$. Accordingly, the maintenance thereof can be facilitated, and a capacity which is sufficient to use for a term of one to several months can be secured. Here, as described later, by providing two filter columns 3 in series, these filter columns 3 can be successively exchanged one by one, and the maintenance performance can be enhanced, and also the filter column 3 at the rear stage can be used to execute the function as the dust monitor 4. That is, the filter column 3 and the dust monitor 4 have the collecting function of dust components and the monitoring function of the collecting capability, and high maintenance performance can be secured with the compatibility between.

The filter element 3a filled in the filter column 3 is preferably made of a polymer material such as polyester or polypropylene as raw material. As in the case of a test result as described later, the adsorption characteristic between the dust components and the polymer material is high, and the surface of the filter element 3a can be kept under the humidified state, particularly under the water coexistent state, so that it can be estimated that the higher collecting capability can be secured. Furthermore, by forming the filter element in the fibrous style or nonwoven cloth style, the surface area can be increased, and the collecting capability can be enhanced. Still furthermore, in some embodiments, the downstream end of the filter element 3a or both the ends of the filter element 3a are held by a precision filter 3b which has the same material as the filter element 3a. For example, the effect of the dust components at the rear stage can be excluded by collecting micro-dust or fly ash of 0.01 µm or more, for example. The container 3c of the filter column 3 is preferably made of polypropylene from the viewpoint of excellent formability, high rigidity and transparency. By increasing the contact time or contact area between the filter element 3a and the sample gas, even in the case of the material having a slightly low capability of holding the humidified state, the collecting capability can be enhanced by filling the filter element 3a in the long filter column 3 or disposing plural filter columns 3 in series.

[Dust Monitor]

In some embodiments, the same column as the filter column 3 is used as the dust monitor 4 at the downstream side of the filter column 3. That is, dust components in stack-gas from a glass fusion furnace or the like contain various kinds of metal oxides, metal halides, etc., and some of these materials are colored compounds. Accordingly, it has been considered to satisfy an object of coloring with dust components transmitted through the filter column 3 and visually checking the coloring. As a result, it has been found that a pollution condition of the filter column 3 can be checked on the basis of the coloring condition of the filter element 3a, the precision filter 3b or the container 3c in the filter column 3, and also the exchange timing of the filter column 3 can be checked on the basis of the coloring condition at the upstream side of the duct monitor 4 which catches and collects the dust components transmitted through the filter column 3. Furthermore, the deterioration condition of the filter column 3 can be also grasped on the basis of the adhesion condition of the dust components on the container surface of the dust monitor 4. Even when the dust components themselves do not contain any colored compound, a component which reacts with a particular component contained in the duct components to be discolored is filled in the dust collecting unit, or the dust collecting unit is subjected to a surface treatment using the component concerned, whereby the function as the dust monitor can be likewise secured. With respect to colorless dust, water droplets, acid mist, etc. adhere to dusts collected by the dust collecting unit, and occurrence of foreign materials is checked at the scene. Accordingly, by checking the occurrence state of foreign materials as described above, the function as the dust monitor can be secured.

Since the dust monitor 4 itself has the function of removing dust components, the effect on the further downstream side can be prevented by exchanging the filter column 3 with the coloring start time set as an exchange timing, whereby it is possible to make the assurance of the function thereof doubly sure. Furthermore, since the dust monitor 4 is identical to the filter column 3, the dust monitor 4 may be shifted to the upstream side and used as the filter column 3, and a new dust monitor 4 may be disposed at the downstream side of the filter column 3, whereby the respective parts can be effectively and practically used.

[Mist Scrubber]

The mist scrubber 5 is a unit containing, and in some embodiments filled with, an element which is formed of an adsorbent and subjected to nonvolatile acid impregnating treatment. A capability of efficiently adsorbing a high concentration of acid mist can be secured by using an adsorbent having a high adsorption capability and a large adsorption surface area such as granular activated charcoal. A porous material such as activated zeolite may be used as the adsorbent in place of activated charcoal. Furthermore, by the nonvolatile acid impregnating treatment, the stability of the adsorbent can be secured without losing the adsorption capability, and $SO_2$, $NO_x$, etc. as measurement target components in stack-gas are prevented from being lost due to the adsorption and also from being lost due to combustion of charcoal or the like under the heating condition. A high concentration of phosphoric acid, a permanganic acid or the like may be used as the nonvolatile acid.

As indicated from the test result which will be described later, the surface of the adsorbent can keep the humidified state under the water-coexistent state, whereby the mist scrubber 5 can secure a higher capability of removing acid mist. The use temperature of the mist scrubber 5 is suitably set to a range from about 80 to 150° C. so as to prevent the coexistent water from being condensed and to reduce the response delay due to adsorption of $SO_2$, $NO_x$, etc. as measurement target components in the stack-gas.

[Mist Monitor]

A unit containing, and in some embodiments filled with, an element formed of perlite type adsorbent is used as the mist monitor 6 at the downstream side of the mist scrubber 5. That is, the perlite type adsorbent has sufficient removing capability of the acid mist of the low concentration as described above. The acid mist adsorbed onto the surface of the adsorbent is gradually bonded with coexisting water and becomes droplets, and the droplets adhere to the surface of the adsorbent or the inner surface of the container filled with the adsorbent. Accordingly, the pollution condition and the exchange timing of the mist scrubber 5 can be grasped by monitoring the adhesion state of the droplets, as described above, in the mist monitor 6 disposed downstream of the mist scrubber 5. Furthermore, the mist monitor 6 itself has the function of removing the acid mist, and thus the mist scrubber 5 can be exchanged without affecting the downstream side of the mist monitor 6.

According to the stack-gas measuring apparatus having the above construction, the continuous measurement having high long-term stability can be performed without being affected by the dust components and the acid mist contained in the stack-gas. Furthermore, the conditions of pollution, etc. of the respective components can be monitored, such an effect as described above can be prevented before it happens, and the continuous measurement having high long-term stability can be performed.

<Another Construction of this Apparatus (Second Construction Example)>

Figure 5:
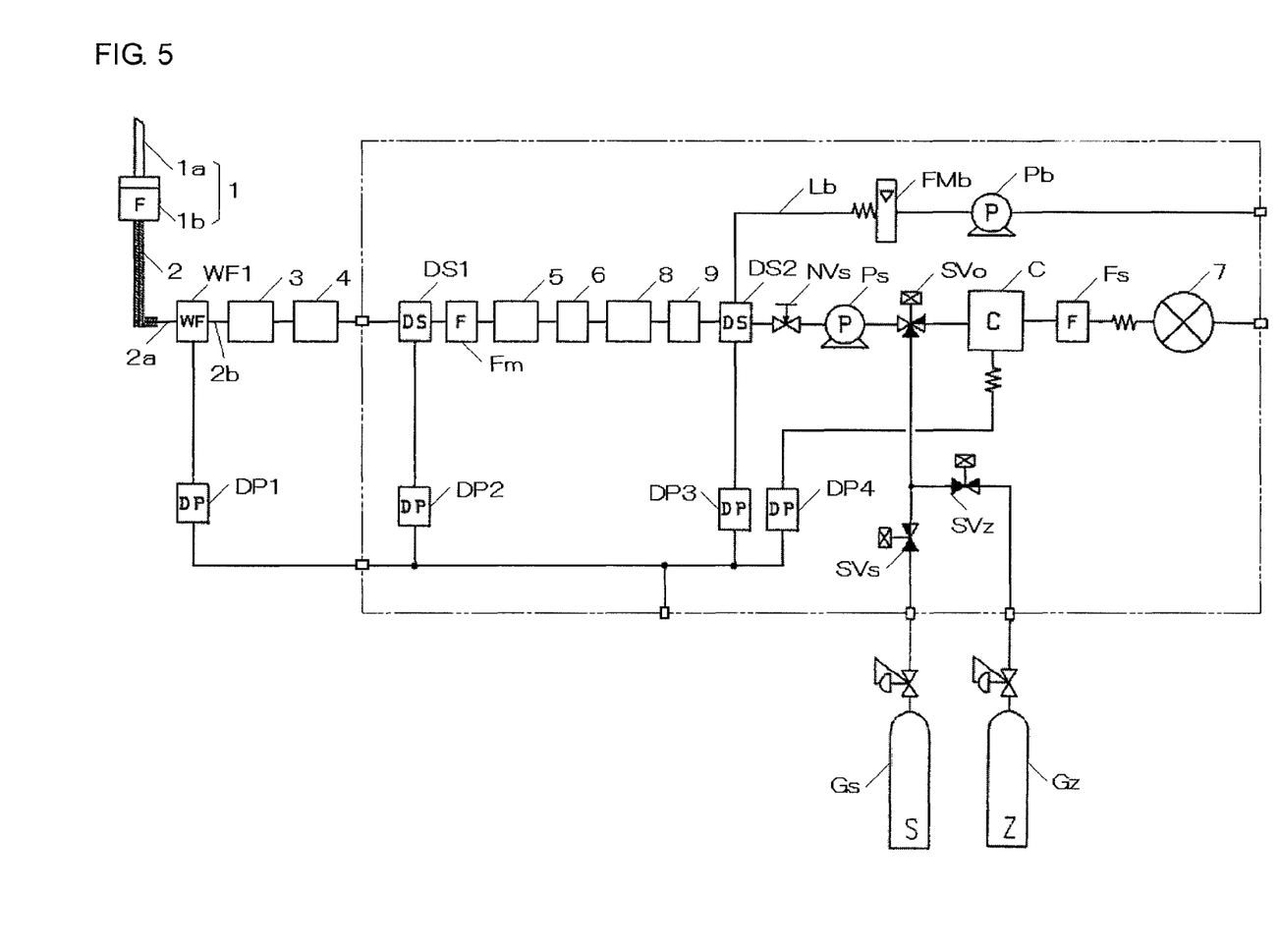
FIG. 5 is a diagram showing a second construction of the stack-gas measuring apparatus according to the present disclosure.

When halogen components are contained in stack-gas, in some embodiments, a halogen collecting unit 8 and a halogen monitor 9 are disposed downstream of the mist monitor 6 in addition to the constituent elements of the first construction example as shown in FIG. 5.

That is, halogen components having strong corrosion behavior may be contained in stack-gas from a glass fusion furnace or the like in addition to dust components and acid mist. These components are not sufficiently removed by the filter column 3 and the mist scrubber 5, and thus it is required to selectively execute a removing treatment on the halogen components without losing $SO_2$, $NO_x$, etc. as measurement target components in the stack-gas.

[Halogen Scrubber]

The halogen scrubber 8 is made of a metal material, and it is preferably formed of a unit containing, and in some embodiments filled with, an element which is subjected to a surface treatment using nonvolatile acid. It is generally difficult to execute a selective adsorption treatment on the halogen components, however, it has remarkably high reactivity with the metal material. Accordingly, by utilizing the characteristics as described above and also using a metal material having a high reactivity for a scrubber base material, the capability of efficiently adsorbing halogen components can be secured. Copper (Cu), tin (Sn), silver (Ag) or the like which is a stable metal as a simple substance and also forms a stable compound as a halide may be used as the metal material. As the property of the element, the metal material as described above may be shaped like wool or carried on an inorganic carrier such as shirasu type natural pumice stone (for example, various particles of 1 to 6 mm in diameter; article name "Pamister" produced by Oue Chemical Industries Co., Ltd., for example) or the like. By the nonvolatile acid impregnating treatment, $SO_2$, $NO_x$, etc. as measurement target components in stack-gas can be prevented from being lost due to adsorption or reaction. Phosphoric acid of a high concentration or permanganic acid may be used as the nonvolatile acid.

[Halogen Monitor]

A unit containing, and in some embodiments filled with, an element formed of a porous material which is subjected to a silver-salt impregnating treatment is used as the halogen monitor 9 at the downstream side of the halogen scrubber 8.

That is, a porous material as an inorganic carrier made of shirasu type natural pumice stone or the like is used as the stable carrier for silver salt, and an impregnating treatment using carbonate silver salt is executed, so that contact and reaction can be performed in a large surface area. Accordingly, there can be formed a monitor having a sufficient detection capability to halogen components passing through the halogen scrubber 8. Here, a halogen $X_2$ reacts with a silver salt contained in the halogen monitor 9 according to the following formula 1, and silver halide (AgX) generated through the reaction is decomposed by light, so that silver is detached and turns black.

$$X_2 + Ag \rightarrow AgX \quad \text{formula 1}$$

Furthermore, the halogen monitor 9 itself has the function of removing halogen components, and thus the halogen scrubber 8 can be exchanged without affecting the downstream side of the halogen monitor 9.

<Another Construction of this Apparatus (Third Construction Example)>

Figure 6:
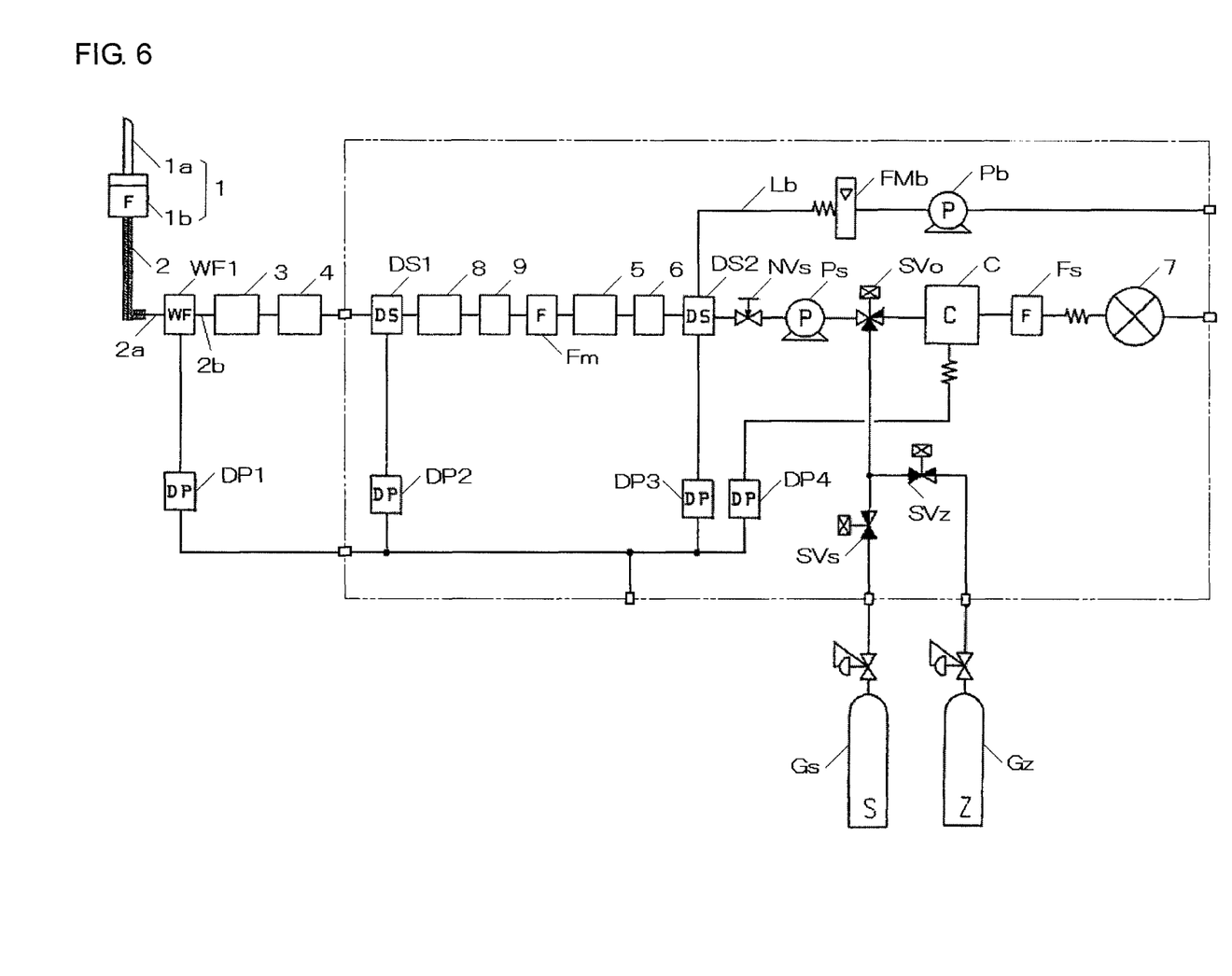
FIG. 6 is a diagram showing a third construction of the stack-gas measuring apparatus according to the present disclosure.

When halogen components are contained in stack-gas and also micro-dust components (particularly metal compound, etc.) exist, in some embodiments, the halogen scrubber 8 and the halogen monitor 9 are disposed at the upstream side of the mist monitor 6 in addition to the constituent elements of the first construction example as shown in FIG. 6.

That is, these components react with one another, and metal halides, etc. are generated and grown, which causes degradation of the collecting capability of the mist scrubber 5. Therefore, the halogen scrubber 8 having high collecting capability to halogens is provided at the upstream side of the mist scrubber 5, whereby occurrence of new dust components can be prevented before it happens and the degradation of the collecting capability of the mist scrubber 5 can be prevented. Furthermore, the halogen scrubber 8 has the function of removing the mist components, and thus the halogen components and the mist components can be simultaneously removed in the halogen scrubber 8 by providing the halogen scrubber 8 at the upstream side of the mist scrubber 5. Accordingly, the load imposed on the mist scrubber 5 provided at the downstream side of the halogen scrubber 8 can be reduced, so that the lifetime of the mist scrubber 5 can be lengthened particularly when high mist stack-gas is targeted.

According to the stack-gas measuring apparatus having the above construction, even when halogen components are contained in stack-gas, the condition of pollution, etc. to the respective components can be monitored, the effect as described above can be prevented before it happens and the continuous measurement having high long-term stability can be performed without being affected by the halogen components.

EXAMPLES

Next, an experiment for inspection was made to inspect causes for inducing problems (problem occurrence causes) of the conventional measuring apparatus and the efficiencies of the respective scrubbers, etc. used for the test of this apparatus when stack-gas from the glass fusion furnace is targeted.

[Test for Inspecting Problem Occurrence Causes in the Conventional Measuring Apparatus]

Properties of Stack-Gas

Properties of stack-gas are varied in accordance with fuel type, a desulfurizing system, the presence or absence thereof, raw material, etc. Properties of stack-gas from a glass fusion furnace were determined as shown in table 1. Here, it has been found that one of the occurrence causes of the problems resides in that dust components such as micro-dust of 0.1 μm or less, acid mist and halogen components cannot be sufficiently determined. For example, it is considered as the occurrence cause of $SO_3$ mist that $SO_3$ mist easily occurs due to decomposition of sodium sulfate ($Na_2SO_4$, decomposition temperature 1350° C.) which is one of the raw materials at the furnace temperature—1600° C. or more in addition to sulfur components in heavy oil as fuel.

Effect of Coexisting Components

It has been found that micro-dust coexists because raw materials become oxides (fly ash) which are vaporized at high temperature and thus it cannot be perfectly removed by an electric dirt collector. Furthermore, it has also been found that the existence of the dust components form harmful materials having strong corrosion behavior and enhanced growth potential through the bonding between the dust components and the acid mist and, further, the bonding of water to the bonded materials concerned. With respect to generation sources of halogen components, fluorine is contained in raw materials such as lime, and chlorine is contained as metal chloride in raw materials.

[Test of Efficiency of Each Scrubber, etc.]

Testing Method

Figure 7:
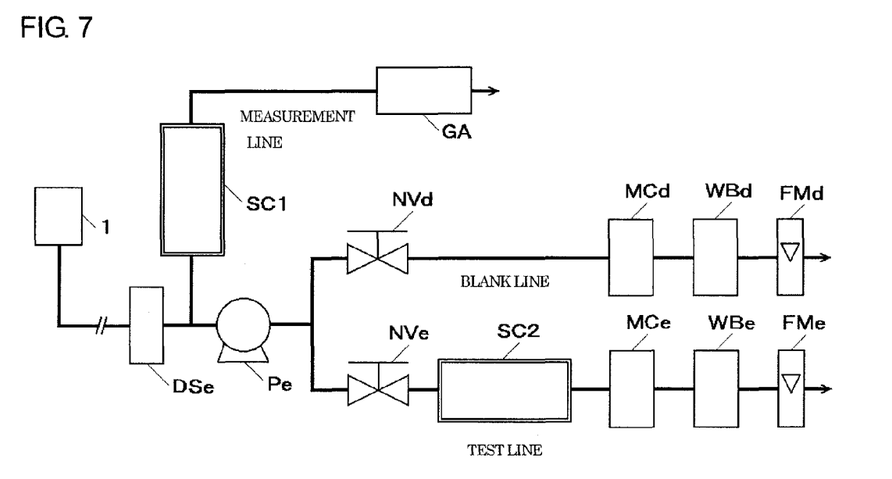
FIG. 7 is a diagram showing a testing method of a scrubber used in the stack-gas measuring apparatus according to the present disclosure.

Stack-gas from a glass fusion furnace using heavy oil containing sulfur components of about 1 to 1.5 wt % as fuel is targeted, and the collecting capability and removing efficiency of various kinds of scrubbers to dust components, acid mist and halogen components were tested by using a testing device such as the testing device shown in FIG. 7. Here, sample gas sucked from the sampling unit 1 was introduced into the drain separator DSe to separate drainage, and then split into two parts. One part (measurement line) was introduced into a measuring apparatus GA (ENDA-640 produced by Horiba Ltd.) being used at the actual place to measure $NO_x$, $SO_2$, CO and $O_2$, and also the other part was introduced to a suction flow passage of the pump Pe.

In the inspection test of the dust components, a scrubber SC1 under test was disposed on a measurement line, and sample gas was continuously introduced into the scrubber SC1 under test at a flow rate of about 3 L/min. Two scrubbers were successively disposed in series in the scrubber SC1 under test, and the collecting capability was determined on the basis of the pollution thereof. The collected dust was subjected to element analysis (scanning electron microscope–energy dispersive X-ray analyzer SEM–EDX produced by Horiba Ltd.) to estimate the origin thereof.

In the inspection test of acid mist and halogen components, the introduced sample gas was further split into two parts. One (blank line) of the two parts was adjusted to about 0.5 L/min by an adjusting valve NVd while the flow rate was checked by a flowmeter FMd, introduced into a mist monitor MCd and further introduced into a pure water bubbler WBd. A solution under the test in which acid mist in the sample gas collected by the mist monitor MCd was dissolved and components dissolved in the pure water bubbler WBd w analyzed to monitor the acid mist collected in the mist monitor MCd and the halogen components dissolved in the pure water bubbler WBd. The other part (test line) was adjusted to about 0.5 L/min by an adjusting valve NVe while the flow rate was checked by a flowmeter FMe, introduced into a scrubber SC2 under test to be treated, introduced into a mist monitor MCe and further introduced into a pure water bubbler WBe. Solution under the test in which acid mist in the sample gas collected by the mist monitor MCe was dissolved and components dissolved in the pure water bubbler WBe were analyzed to monitor the acid mist and the halogen components passing through the scrubber under test.

(2) Test Condition (2-1) As the scrubber for the dust components, (i) a filter column (FC) filled with 15 layers of polyester fiber filters, and (ii) a column filled with quartz wool were used.

(2-2) As the scrubber for the acid mist and the halogen compounds, (i) the mist scrubber of this apparatus (MS, heated at about 90° C.), (ii) a unit filled with an element formed of perlite type adsorbent (SU, heated at about 90° C.), and (iii) a halogen scrubber of this apparatus (HS, normal temperature) for reference: with a halogen monitor (HM, normal temperature) were used.

(2-3) The quantity of the acid mist was calculated on the basis of a measurement result (IC analysis) of the components dissolved in the mist monitor MCe by an ion chromatography (model type 861 produced by Metrome company).

(2-4) The quantity of the halogen components was calculated on the basis of a measurement result (IC analysis) of the components dissolved in the pure water bubblers WBd and WBe by the ion chromatography (model type 861 produced by Metrome company).

(3) Test Result (3-1) Analysis of dissolved gas components in stack-gas

As an analysis of dissolved gas components in non-processed stack-gas, after the sample gas was introduced into the blank line for about two hours, the solution of the pure water bubbler WBd was subjected to IC analysis. Furthermore, the gas components in the stack-gas from which respective ion components were derived were estimated. Existence of $SO_3$ mist and nitric mist as acid mist and existence of HF, HCl and $Cl_2$ as halogen components are estimated.

(3-2) Adsorption Test of Filter Column

With respect to the collecting capability of each scrubber to dust components after stack-gas was continuously sucked for about one week in the measurement line, as shown in the following table 1, it has been found that the dust components are little collected by the quartz wool, but the polyester fiber filter (FC) has a high collecting capability. Furthermore, the main component of coloring dusts is $SiO_2$, and it is estimated that $SiO_2$ is derived from ash of a raw material.

TABLE 1

| Type and name of scrubber | | Coloring or non-coloring (Determination after one week) | Component analysis of adhering dust |
|---|---|---|---|
| Blank | — | — | — |
| FC | Filter column | Maize | Coloring dust is determined as $SiO_2$ |
| HS | Halogen scrubber | Colorless | No coloring and no pollution |

(3-3) $SO_3$ Mist Removing Performance Test of Mist Scrubber

With respect to the removing capability of each scrubber to acid mist after stack-gas was continuously sucked in the test line for about one week, it has been found that the removal rate sticks around about 70% in the case of the perlite type adsorbent (SU), however, the mist scrubber (MS) has a high removing capability of about 97%. For reference, the halogen scrubber (HS) has a removal rate of about 83%, and the validity of the addition of the halogen scrubber in the second and third construction examples of this apparatus to the acid mist was verified.

TABLE 2

| Type and name of scrubber | | IC analysis concentration ratio (%) of $SO_4^-$ collected by mist monitor | Removal rate (%) |
|---|---|---|---|
| Blank | — | 100 | 0 |
| MS | Mist scrubber | 3 | 97 |
| HS | Halogen scrubber | 17 | 83 |
| SU | Adsorbent unit | 30 | 70 |

(3-4) Removing Performance of Halogen Gas of Halogen Scrubber

With respect to the removing capability of each scrubber to the halogen components after stack-gas was continuously sucked in the test line for about one week, as shown in the following table 3, it has been found that the removal rate sticks around 55%/0% for HF/HCl ($Cl_2$) in the case of perlite type adsorbent (SU), and the halogen scrubber (HS) has a high removal capability of 100%/80%. For reference, the mist scrubber (MS) has a removal rate of 66%/0%, and it has been found that the HF removing capability of the mist scrubber provided at the upstream side of the halogen scrubber can contribute to increase of the lifetime of the halogen scrubber in the second construction example of this apparatus.

TABLE 3

| Type and name of scrubber | | IC analysis concentration ratio (%) of HF/HCL ($Cl_2$) in pure water bubbler | Comparison of removal rate (%) |
|---|---|---|---|
| Blank | — | 100/100 | 0/0 |
| MS | Mist scrubber | 34/100 | 66/0 |
| HS | Halogen scrubber | 0/20 | 100/80 |
| SU | Adsorbent unit | 45/100 | 55/0 |

(3-5) Others

As a result of the above inspection test, it has been verified that the respective scrubbers, etc. have high collecting capabilities and high removal rates for respective components of dust, mist and halogen, and at the same time it has been verified that these scrubbers can complement the collecting capabilities and the removable capabilities of the respective components with one another by disposing these scrubbers in combination. That is, this apparatus has remarkably high usability in the point that it is not limited to a mere combination of the respective scrubbers, etc., but can constitute a high-function sample treatment unit having compositely high collecting capability and removing capability.

As described above, some embodiments may be mainly applied to the measuring apparatus and method for measuring specific components in stack-gas from a glass fusion furnace. However, other embodiments of the measuring apparatus and method of the present disclosure are applicable to stack-gas from a diesel electric power generator following high-temperature combustion, sulfuric acid plants, metal refining (sulfide ash incinerator), etc.

It should be understood that the embodiments herein are illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. A stack-gas measuring apparatus which targets a stack-gas containing dust components and acid mist, comprising:

a sample introducing unit for introducing the stack-gas;

a cooling unit in which dust components are agglomerated, wherein the cooling unit comprises a dust removing unit, and wherein the dust removing unit is configured to remove dust components agglomerated in the cooling unit during cooling;

a mist collecting unit which is provided downstream of the dust removing unit and which contains an adsorbent for removing acid mist in the stack-gas; and an analyzer into which treatment gas clean-treated by the respective units is introduced to measure a gas component in the stack-gas.

2. The stack-gas measuring apparatus according to claim 1, further comprising a mist monitor containing an adsorbent downstream of the mist collecting unit, wherein the dust removing unit functions as a monitor of a pollution state of the dust components.

3. The stack-gas measuring apparatus according to claim 1 wherein the stack-gas measuring apparatus has a measurement target sample comprising halogens or halides, further comprising a halogen collecting unit for removing halogens or halides disposed downstream of the mist collecting unit or a mist monitor, and a halogen monitor which contains an element formed of porous material containing coloring material disposed downstream of the halogen collecting unit.

4. The stack-gas measuring apparatus according to claim 1 wherein the stack-gas measuring apparatus has a measurement target sample comprising halogens or halides, further comprising a halogen collecting unit for removing halogens or halides provided upstream of the mist collecting unit.

5. A stack-gas measuring method which targets a stack-gas comprising dust components and acid mist the method comprising:

subjecting sampled stack-gas to a primary treatment to remove the dust components under coexistence with water by a dust removing unit;

subjecting the sampled stack-gas to a secondary treatment to remove the acid mist by a mist collecting unit;

subjecting the sampled stack-gas to a tertiary treatment to remove halogens or halides by a halogen collecting unit when the sampled stack-gas further comprises the halogens or the halides; and measuring a gas component in the sampled stack-gas which has been subjected to the primary and secondary treatments or the primary to tertiary treatments.

* * * * *